United States Patent [19]
Pihl et al.

[11] Patent Number: 4,870,341
[45] Date of Patent: Sep. 26, 1989

[54] IMPEDANCE MEASUREMENT CIRCUIT

[75] Inventors: James M. Pihl, Bothell; Denny C. Edwards, Bellevue, both of Wash.

[73] Assignee: First Medical Devices Corporation, Bellevue, Wash.

[21] Appl. No.: 228,330

[22] Filed: Aug. 3, 1988

Related U.S. Application Data

[62] Division of Ser. No. 935,248, Nov. 26, 1986, Pat. No. 4,785,812.

[51] Int. Cl.⁴ ................. A61N 1/00; H05G 00/00
[52] U.S. Cl. ..................... 324/57 R; 128/419 D; 128/734
[58] Field of Search ............ 128/419 D, 419 PT, 734; 324/62 R, 57 R

[56] References Cited

U.S. PATENT DOCUMENTS

| | | | |
|---|---|---|---|
| 4,080,562 | 3/1978 | Rubel et al. | 324/62 |
| 4,164,215 | 8/1979 | Finlayson et al. | 128/419 D |
| 4,319,241 | 3/1982 | Mount | 324/62 |
| 4,328,808 | 5/1982 | Charbonnier et al. | 128/419 D |
| 4,337,776 | 7/1982 | Daly et al. | 128/419 PT |
| 4,771,781 | 9/1988 | Lerman | 128/419 D |

Primary Examiner—Francis Jaworski
Assistant Examiner—George Manuel
Attorney, Agent, or Firm—Seed and Berry

[57] ABSTRACT

A protection circuit for a defibrillator that prevents a defibrillator pulse from being generated if the impedance between the defibrillator's electrode leads is not characteristic of the impedance between a pair of defibrillator electrodes properly connected to the defibrillator. The impedance measuring circuit applies a current to the electrode leads and the resulting voltage is measured to provide an indication of the electrode's impedance. The current is applied between the electrodes at about 33 kHz to approximate the impedance between a pair of defibrillator electrodes during a defibrillation pulse. The output of the measurement circuit is converted to an 8 bit word by an analog-to-digital converter and read by a microprocessor which compares the measured impedance to various impedance values in order to either generate an enable signal for the defibrillator or display messages indicative of open or short circuited electrode leads or a patient monitoring electrode connected to the electrode leads. The impedance measurement circuit operates in either of two ranges which are selected by the microprocessor on the basis of the measured impedance values.

6 Claims, 3 Drawing Sheets

IMPEDANCE MEASUREMENT CIRCUIT

This application is a divisional of U.S. patent application Ser. No. 935,248, filed Nov. 26, 1986, now U.S. Pat. No. 4,785,812.

TECHNICAL FIELD

This invention relates to defibrillators that both defibrillate and monitor through a common set of electrode leads and, more particularly, to a system for preventing defibrillation in the event that the leads are connected to an incorrect electrode or are improperly connected to a defibrillation electrode.

BACKGROUND ART

Defibrillators have long been used in the field of medicine to shock the heart into operating in a normal sinus rhythm when the heart goes into fibrillation. Defibrillators function by applying a relatively high powered pulse at a relatively high voltage between a pair of defibrillation electrodes that are placed against the chest of a patient. The relatively high power, high voltage characteristics of the defibrillation pulse require special electrodes that, among other things, provide a relatively large area of contact between the electrodes and the patient. For this reason, defibrillation electrodes are relatively expensive, typically selling to the end user at between $10 and $20 each.

It is often difficult to determine whether a patient is in need of defibrillation. An examination of the patient's electrocardiogram (ECG) is often helpful in making this determination. Consequently, many defibrillators include an ECG monitor and associated circuitry to obtain an ECG of the patient. The ECG monitor is normally connected to a pair of patient monitoring electrodes that adhere to the chest of the patient. The monitoring electrodes generate relatively low voltage, extremely low power, electrical signals indicative of the activity of the heart. The low voltage, low power characteristics of the signals generated by the monitoring electrodes, in contrast to the high voltage, high power pulses delivered to defibrillation electrodes, make monitoring electrodes substantially different from defibrillation electrodes. Monitoring electrodes typically have a relatively small area of contact with the patient, they are usually used once and then disposed of and they normally cost about 50¢.

Monitoring electrodes are not suitable for use as defibrillation electrodes for several reason. For example, the relatively small contact area between the monitoring electrode and the patient would result in extremely high current densities if a defibrillation pulse was applied to the monitoring electrode. The high current density would severely burn the patient. Defibrillation electrodes are not normally used for patient monitoring because of their relatively high cost.

When an emergency health care practitioner responds to a cardiac emergency, he or she normally obtains the patient's ECG to determine if defibrillation is necessary. In many circumstances, defibrillation is not required. Thus, in most circumstances, a patient monitoring electrode is used, and the defibrillation electrodes are not required. If defibrillation is required, the health care practitioner must attach defibrillation electrodes to separate electrode leads or they must remove the patient monitoring electrode from the electrode leads and reconnect the defibrillation electrodes to the leads. Each of these procedures has a significant disadvantage.

The emergency conditions under which defibrillation normally occurs makes inadvertent defibrillation through patient monitoring electrodes quite possible. As mentioned above, the practitioner will initially connect the electrode leads to a patient monitoring electrode in order to obtain an ECG. If an emergency condition, e.g., fibrillation, then occurs, it is quite possible for the practitioner to forget that the defibrillator is connected to monitoring electrodes in the excitement of the emergency. In an effort to respond to the emergency as quickly as possible, the emergency health care practitioner may cause the defibrillator to generate a defibrillation pulse while the electrode leads are still connected to the monitoring electrode.

The danger of defibrillating through patient monitoring electrodes is even more acute because of the advent of automatic and semiautomatic defibrillators used by relatively untrained personnel. Most cardiac emergencies occur outside the presence of trained health care personnel. Recognizing that defibrillation must occur very shortly after the onset of fibrillation if it is to be successful, automatic and semiautomatic defibrillators have been proposed in order to allow even untrained personnel to defibrillate. In automatic or semiautomatic defibrillators, the patient's ECG is monitored and the defibrillator itself determines from the characteristics of the ECG whether defibrillation is required. In the automatic defibrillator, the defibrillator automatically generates a defibrillation pulse when defibrillation is required. In the semiautomatic model, the defibrillator informs the practitioner that defibrillation is required. The practitioner then manually triggers the defibrillator pulse. It is highly desirable in the case of a semiutomatic defibrillator, and absolutely required in the case of an automatic defibrillator for the defibrillator to determine whether it is connected to a defibrillation electrode. Obviously an automatic defibrillator should not generate a defibrillation pulse if it is connected to a monitoring electrode. While it is possible for an operator of a semiautomatic defibrillator to ensure that the defibrillator is connected to a defibrillation electrode prior to manually generating the defibrillation pulse, the relatively untrained nature of semiautomatic defibrillation operators makes the likelihood of mistake relatively high. Consequently, even for semiautomatic defibrillators, it is highly desirable for the defibrillator to be disabled from generating a defibrillation pulse if a patient monitoring electrode is connected to the defibrillator.

In addition to the problems resulting from attempting defibrillation through patient monitoring electrodes, problems also exist when defibrillation is attempted through improperly connected defibrillator or patient monitoring electrodes. If the electrode leads are short-circuited to each other when defibrillation is attempted, the relatively high current flow occurring through the short circuit can damage the defibrillator. More significantly, the short circuit prevents the defibrillation pulse from reaching the patient, thus making defibrillation impossible. Likewise, if the electrodes are not properly connected to the electrode leads, an open circuit condition can exist which also prevents the defibrillation pulses from reaching the electrodes. Consequently, automatic and semiautomatic defibrillators are not practical unless the defibrillator can determine for itself whether the defibrillator is properly connected to defibrillation electrodes.

DISCLOSURE OF THE INVENTION

It is an object of the invention to provide a defibrillator that may be used by relatively untrained personnel without the risk of attempting defibrillation through patient monitoring electrodes.

It is another object of the invention to provide a protective circuit to allow an automatic or semiautomaiic defibrillator to both monitor and defibrillate through common electrode leads.

It is another object of the invention to provide a defibrillator that will not attempt to defibrillate in the event that either an electrode is improperly connected to the electrode leads or the electrode leads have become shorted.

It is still another object of the invention to provide an accurate, relatively inexpensive impedance measuring circuit for generating a signal indicative of the impedance between a pair of defibrillation electrodes during a defibrillation pulse.

It is a further object of the invention to provide an impedance measuring circuit that is automatically switched to one of two operating ranges, depending upon the value of the measured impedance.

These and other objects of the invention are provided by a protective circuit for a defibrillator having an enable input allowing defibrillation when an enable signal is applied to the enable input. The protective circuit includes an impedance measuring circuit connected between the defibrillators electrode leads. The impedance measuring circuit generates an output signal indicative of the impedance between the electrodes. A processor receives the output of the impedance measuring circuit and generates the enable signal when the output signal is indicative of an impedance within a range of impedances characteristic of defibrillator electrodes properly connected to the electrode leads. The impedance measurement circuit includes an AC current source connected between the electrode leads so that the voltage across the leads is proportional to the impedance between the electrodes. The frequency of the AC signal is preferably about 33 kHz to approximate the impedance between the defibrillator electrodes during a defibrillation pulse. In order to increase the range and sensitivity of the impedance measuring circuit, the circuit operates in one of two ranges, depending upon the measured impedance. In a low impedance range, the output of the impedance measuring circuit is a relatively large multiple of the measured impedance. In the high impedance range, the output of the impedance measuring circuit is a relatively low multiple of the measured impedance. The processor preferably includes an analog-to-digital converter receiving the output of the impedance measurement circuit and generating a binary coded signal indicative of the measured impedance. The binary coded signal from the analog-to-digital converter is applied to a microprocessor that determines the impedance and generates the enable signal when the impedance is within the proper range for defibrillation through an enable signal generating algorithm. The processor may also generate a visual message whenever the measured impedance is indicative of either an open circuit, a short circuit, a patient monitoring electrode connected to the electrode leads, or the impedance is between the ranges indicative of defibrillator electrodes or monitor electrodes.

BEST MODE FOR CARRYING OUT THE INVENTION

Figure 1:
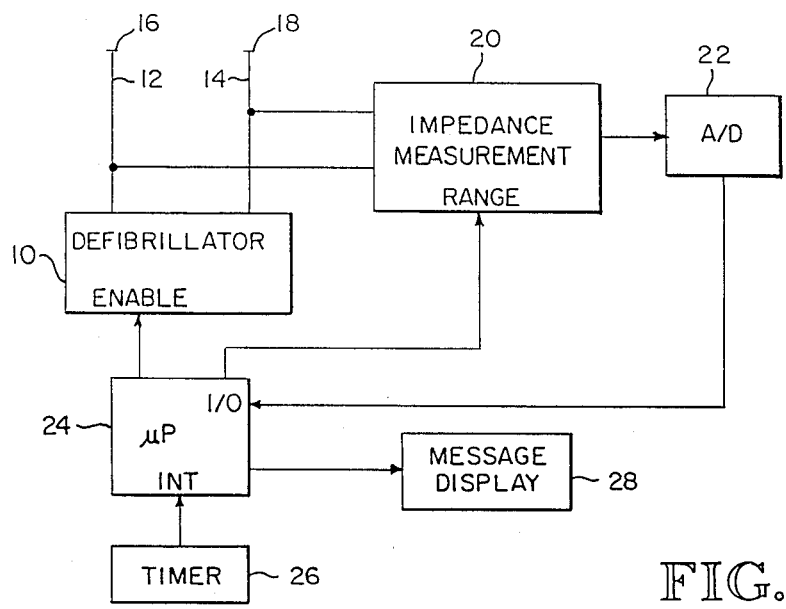
FIG. 1 is a block diagram of a defibrillator employing the protection system for preventing defibrillation when the defibrillator is either improperly connected to electrodes or connected to the incorrect electrodes.

A defibrillator incorporating the protective system is illustrated in FIG. 1. A defibrillator 10 is of the conventional variety having a pair of electrode leads 12, 14, connected to electrodes 16, 18, respectively. The electrodes 16, 18 are normally special purpose defibrillator electrodes when the defibrillator 10 is to be used to defibrillate a patient. However, the electrodes 16, 18 are normally patient monitoring electrodes when the defibrillator 10 contains an ECG monitor and is being used to monitor the condition of the patient before defibrillation. In the event that the conventional defibrillator 10 does not include an enable input, an enable input can be easily implemented by one skilled in the art. For example, an appropriate semiconductor switch can be placed in series or parallel with the normal, manually actuated switch of the defibrillator.

An impedance measurement circuit 20, described in greater detail below, is connected between the electrode leads 12, 14. The impedance measuring circuit 20 applies an analog signal to a conventional analog-to-digital converter 22 indicative of the impedance between the electrodes 16, 18 The impedance measuring circuit 20 is abe to determine the impedance between electrodes 16, 18 by measuring the impedance between the leads 12, 14, since the impedance looking into the defibrillator 10 is normally substantially greater than the impedance between the electrodes 16, 18. The impedance measuring circuit 20 operates in one of two ranges, depending upon the condition of a two bit binary signal applied to the impedance measuring circuit 20 by a properly programmed microprocessor 24. The microprocessor 24 receives an eight bit digital word indicative of the impedance between the electrodes 16, 18 from the analog-to-digital converter 22.

Although the microprocessor 24 may operate in a variety of modes depending upon its programming, in the embodiment of FIG. 1 it is interrupt driven each time a conventional timer 26 generates an interrupt pulse which is applied to the interrupt port of the microprocessor 24. When the microprocessor 24 is periodically interrupted, it executes an interrupt subroutine that determines the impedance indicated by the 8 bit word from the analog to digital convertor 22 and then switches the impedance measuring circuit 20 to the proper range, if required. If the impedance is within the range of impedances characterized by the impedance between a pair of properly connected defibrillation electrodes (i.e., normally 30–200 ohms), the impedance measuring circuit 20 also applies an enable signal to the enable input of the defibrillator 10. If the impedance between the electrode 16, 18 is within the range characteristic of a patient monitoring electrode (i.e., normally 300–2,000 ohms), the microprocessor 24 applies an appropriate signal to a message display device 28 to inform the operator that patient monitoring electrodes are connected to the defibrillator 10. If the measured impedance is below the impedance that is normally between a pair of properly connected defibrillation electrodes (i.e., less than 30 ohms), the microprocessor 24 inhibits the unit from generating a defibrillation pulse. Finally, if the measured impedance is of a value normally characteristic of an open circuit (i.e., in excess of 2,000 ohms), the microprocessor 24 generates a signal causing the message display device 28 to inform the operator that the electrodes 16, 18 are not properly connected to the defibrillator 10. The message display unit 28 may assume a variety of forms. In its most simple form, it may merely be three light emitting diodes each of which are illuminate to display respective "open circuit," "short circuit," "patient monitor electrodes" and "defibrillation electrodes" messages.

A fourth mode exists between defibrillator and monitor electrode impedance ranges (200 ohms to 300 ohms) when the message "check electrodes" is enabled.

Figure 2:
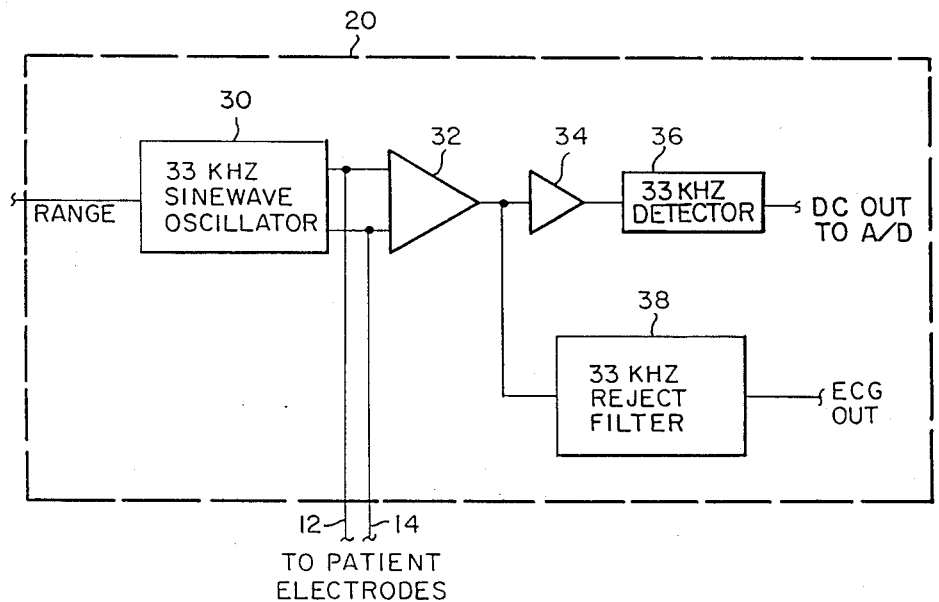
FIG. 2 is a block diagram of an impedance measuring circuit used in the protection system of FIG. 1.

A block diagram of the impedance measuring circuit 20 is illustrated in FIG. 2. A 33 kHz sine wave oscillator 30 having a relatively high output impedance is connected between the electrode leads 12, 14. Since the output impedance of the oscillator 30 is substantially greater than the impedance between the leads 12, 14 under all but open circuit conditions, the oscillator 30 functions as a 33 kHz current source. The voltage between the electrodes 12, 14 is thus representative of the impedance between the electrode leads 12, 14, since the inter-electrical voltage is equal to the product of the current (which is constant for each range) and the inter-electrical impedance.

The oscillator 30 operates in either of two ranges, depending upon the range input applied to the impedance measurement circuit 20 by the microprocessor 24 (FIG. 1). The use of two ranges allows the measurement circuit 20 to achieve good sensitivity while measuring impedance over a relatively wide range as explained in greater detail below.

The electrode leads 12, 14 are also connected to an instrumentation amplifier 32 generating an output that is proportional to the voltage between the leads 12, 14 while providing good common mode rejection of signals applied equally to both of the leads 12, 14. The input impedance of the instrumentation amplifier 32 is substantially greater than the impedance between the electrode leads 12, 14 when they are connected to even a patient monitoring electrode so that substantially all of the current generated by the oscillator 30 flows through the leads 12, 14 and the electrodes to which they are connected rather than through the input terminals of the instrumentation amplifier 32.

The output of the instrumentation amplifier 32 is further boosted by a 33 kHz amplifier 34 which increases the signal-to-noise ratio of the signal by attenuating frequency components outside the 33 kHz frequency range generated by the oscillator 30. The output of the amplifier 34 is converted to a DC voltage proportional to the magnitude of the AC signal at the output of amplifier 32 by a 33 kHz detector 36. The output of the detector 36 is thus a DC signal having an amplitude that is proportional to the impedance between the electrodes 12, 14.

The output of the instrumentation amplifier 32 is also applied to a 33 kHz reject filter 38 that removes the 33 kHz frequency component from the signal at the output of the instrumentation amplifier 32. The output of the 33 kHz reject filter 38 may be applied to a conventional ECG monitor in order to monitor the condition of the patient prior to defibrillation. Since the defibrillator 10 (FIG. 1) is also connected to the electrode leads 12, 14, it is apparent that both defibrillation and patient monitoring occurs through the same electrode leads 12, 14.

As mentioned above, the use of multiple ranges in the impedance measurement circuit 20 increases the range and sensitivity of the measurement circuit as compared to a single range instrumentation circuit. Let us assume, for example, that the measurement circuit is to measure impedances between 30 ohms and 2k and that the voltage at the output of the detector 36 is to vary between 0–10 volts. Under these circumstances, the output of the detector 36 with a measured impedance of 2kHz would be ten volts so that the sensitivity expressed in volts per ohm would be $5 \times 10^{-3}$. An impedance of 30 ohms would thus result in an output voltage of 0.15 volt. An impedance of 40 ohms would result in an output voltage of 0.2 volt. There would thus be only 0.05 volt separating measured impedances of 30 and 40 ohms. By using two ranges, the output of the detector 36 can vary by ten volts between 30 and 200 ohms and between 300 ohms and 2k. Thus, in the low impedance range, the voltage at the output of detector 36 will be 10 volts at 200 ohms, thus yielding a sensitivity of $5 \times 10^{-2}$ volts per ohm. A measured impedance of 30 ohms would thus generate an output voltage of 1.5 volt. A measured impedance of 40 ohms would generate an output voltage of 2 volts. Thus, in the low range, the output voltage separating measured impedances of 30 and 40 ohms would be 0.5 volt in contrast to the 0.05 volt separating the measured impedances of 30 and 40 ohms in the single range example given above. It is thus seen that the use of two ranges provides greater sensitivity, yet still allows the impedance measuring circuit 20 to measure the same range of impedances. The above impedance and voltage examples are provided merely for illustrative purposes, it being understood that the principle remains the same regardless of the number of measurement ranges, measurement sensitivities expressed in volts per ohm, and output voltage limits that are used in the measurement circuit.

Figure 3:
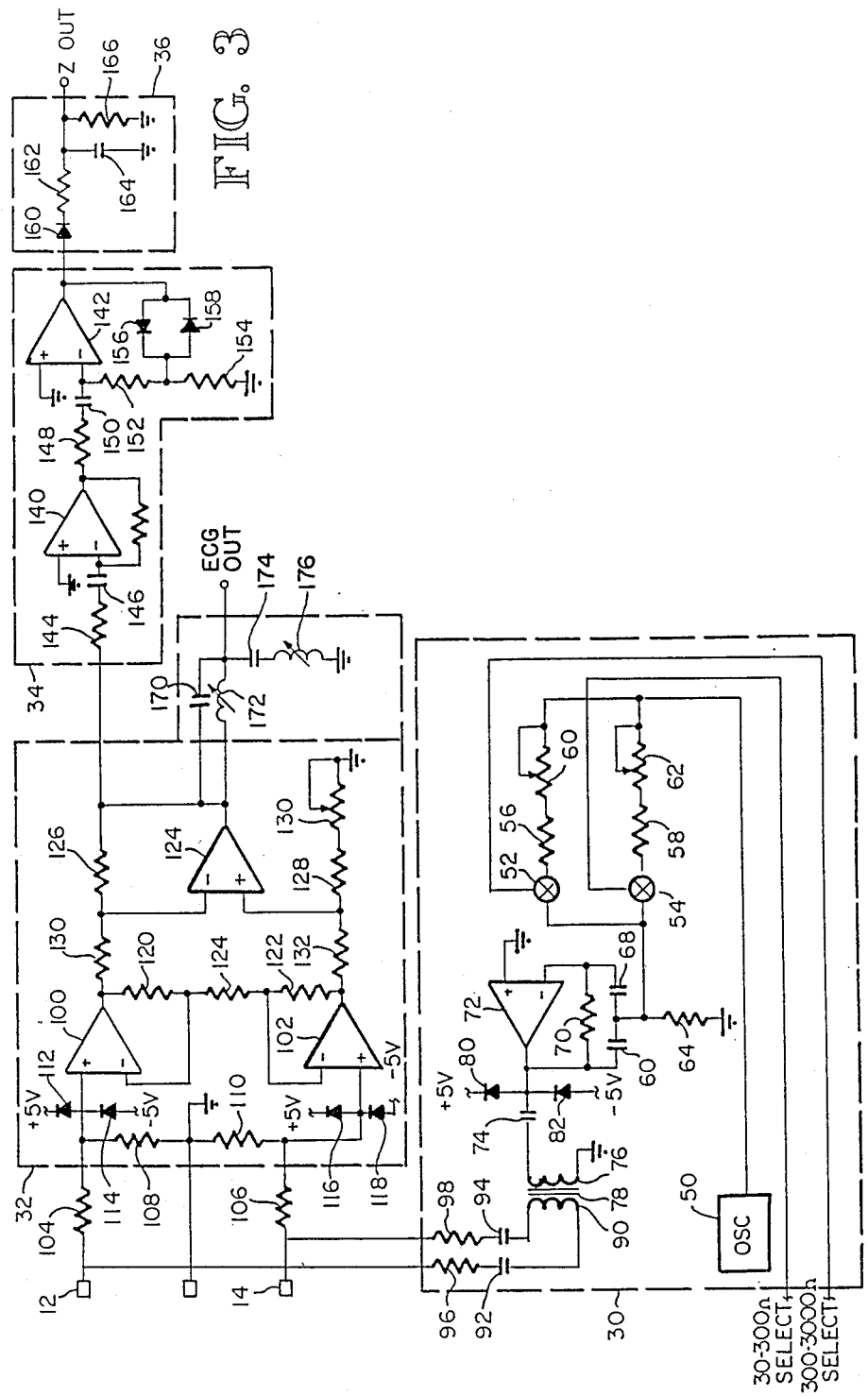
FIG. 3 is a schematic of the impedance measuring circuit of FIG. 2.

A schematic of the measurement circuit 20 illustrated in FIG. 2 is shown in FIG. 3. The oscillator 30 includes a conventional 33 kHz square wave oscillator 50 which may be of a conventional design such as an astable multivibrator circuit. The oscillator 50 generates a 33 kHz square wave varying between 0 and 5 volts. The output of the oscillator 50 is applied to a pair of conventional solid state CMOS switches 52, 54 through respective resistors 56, 58 and potentiometers 60, 62. As explained in greater detail below, the resistor 56 has a value ten times larger than that of resistor 58. Similarly, potentiometer 60 has a value that is ten times the value of potentiometer 62. As a result, when switch 52 is closed responsive to the high impedance range being selected, the oscillator generates a signal having an amplitude that is ten times smaller than when switch 54 is closed responsive to the low impedance range being selected.

The outputs of the switches 52, 54 are tied together and applied to the junction of resistor 64, capacitor 60, and capacitor 68 which, in combination with feedback resistor 70 and operational amplifier 72, implement a high active band-pass filter centered at the 33 kHz frequency of the signal generated by the oscillator 50. The outputs of the amplifier 72 are applied through an AC coupling capacitor 74 to the primary 76 of a transformer 78. Capacitor 74 is provided to block DC offsets at the output of amplifier 72 from flowing through the primary 76 of the transformer 78 and thus saturating the core of the transformer 78. A pair of diodes 80, 82 are provided to clamp the output of the amplifier 72 at approximately +5.7 volts and −5.7 volts to protect the amplifier 72 when a defibrillation pulse is applied to the electrode leads 12, 14.

The high Q of the amplifier 72 causes a 33 kHz sinewave to be generated at the secondary 90 of transformer 78 which is applied through coupling capacitors 92, 94 and resistors 96, 98 to the electrode leads 12, 14. The resistors 96, 98 have a value that is substantially larger than the impedance of even patient monitoring electrodes such as, for example, 20 k ohms. Similarly, the coupling capacitors 92, 94 can have a relatively large impedance, such as 10 k ohms at 33 kHz. As a result, the current flowing through the secondary 90 of transformer 78 is relatively insensitive to the impedance of the electrodes connected between the electrode leads 12, 14, so that the oscillator 30 functions as an AC current source.

The instrumentation amplifier 32 employs a pair of operational amplifiers 100, 102 having their non-inverting inputs connected to respective electrode leads 12, 14 through respective resistors 104, 106. Resistors 108, 110 are connected to amplifiers 100, 102, respectively, to reference their inputs to ground. Diodes 112, 114, 116, 118 are provided to clamp the inputs of the amplifiers 100, 102 at approximately +5.7 volts and −5.7 volts. Feedback resistors 120 and 122, in combination with resistor 124 set the gain of the amplifiers 100, 102 at 2.

The outputs of the amplifiers 100, 102 are applied through respective resistors 130, 132 to the inputs of an operational amplifier 124 having its gain set at unity by a feedback resistor 126. Resistor 128, in combination with potentiometer 130, is adjusted to equal the impedance of resistor 126 to provide good, common mode rejection. The output of the amplifier 124 thus constitutes the output of the instrumentation amplifier 32 (FIG. 2).

As mentioned above, the output of the instrumentation amplifier 32 is applied to a 33 kHz amplifier 34 and to a 33 kHz reject filter 38. The 33 kHz amplifier 34 is implemented by two operational amplifiers 140, 142 each having a lead network consisting of resistor 144 and capacitor 146 for amplifier 140 and resistor 148 and capacitor 150 for amplifier 142. Although the amplifiers 140, 142 have a gain of zero at DC, the gain of amplifier 140 is approximately 10 at the 33 kHz operating frequency. Similarly, amplifier 142 has a gain of approximately 10 as determined by feedback resistor 152 and resistor 148. Diode 156 is provided to compensate for the forward drop of diode 160 in the detector circuit 36. Diode 158 prevents the output of amplifier 142 from swinging to the negative rail and causing reduced frequency response characteristics. When the output of amplifier 142 is positive, current flows through diode 160 and resistor 162 to charge capacitor 164 positively. Resistor R154 causes a current to flow through diode 156 equal to the current flowing through diode 160. This causes the forward voltage drops through both diodes to be approximately the same. Resistor 166 is provided to allow capacitor 164 to discharge since the diode 160 prevents the capacitor 164 from otherwise discharging. Capacitor 164 thus charges to a value that is proportional to the peak amplitude of the 33 kHz signal applied to the 33 kHz amplifier 34. The gains of the various amplifiers are set so that the output of the 33 kHz detector 36 is one volt when the impedance between the leads 12, 14 is 100 ohms in the low range and 1,000 ohms in the high range. As a result, for a given range of voltages at the output of the detector 36, the impedance measurement circuit 20 can measure an impedance ten times greater in the high impedance range than in the low impedance range.

The 33 kHz reject filter 38 is required to remove a relatively large 33 kHz signal from the relatively low amplitude ECG signal on the electrode leads 12, 14. The output of the amplifier 124 is initially applied to a parallel tank circuit consisting of capacitor 170 and inductor 172 which together have a relatively high parallel impedance at their 33 kHz resonant frequency. A series resonant circuit consisting of capacitor 174 and inductor 176 has a relatively low series impedance at their 33 kHz resonant frequency. As a result, capacitor 170 and inductor 172 substantially block the 33 kHz signal and capacitor 174 and inductor 176 shunt the remaining 33 kHz signal to ground. The resulting signal has a much attenuated 33 kHz component.

Figure 4:
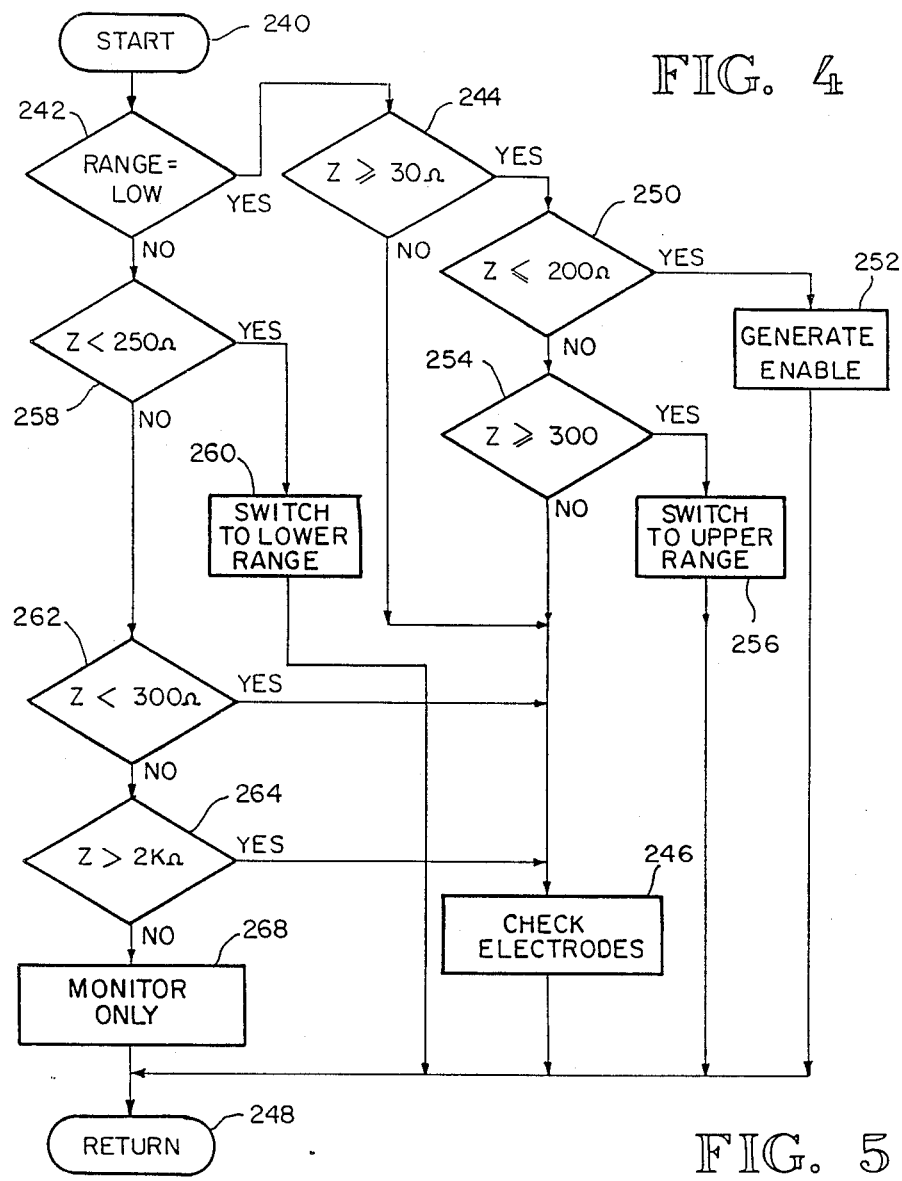
FIG. 4 is a flow chart of the software used to program a microprocessor used in the protection system of FIG. 1.

A flow chart for controlling the operation of the microprocessor 24 (FIG. 1) is illustrated in FIG. 4. As indicated above, the microprocessor is periodically interrupted by interrupt pulses from a conventional timer 26. The microprocessor 24 then executes an interrupt subroutine that starts at 240. The program then determines at 242 whether the impedance measurement circuit 20 is operating in the low impedance range. If so, the interrupt routine branches to 244 where the 8 bit word from the A/D converter 22 is read and the indicated impedance is compared to 30 ohms. If the measured impedance is less than 30 ohms, there may very well be a short circuit in the electrode leads 12, 14. As a result, the microprocessor 24 outputs a message display bit at 246 to inform the user to check the electrodes. The interrupt routine then returns to main program or waits for the next interrupt at 248.

In the event that the impedance is found to be larger than 30 ohms at 244, the routine branches to 250 where the measured impedance from the A/D converter 22 is compared to 200 ohms. If the measured impedance is less than 200 ohms, the impedance between the electrode leads 12, 14 must be between 30 and 200 ohms. An impedance in this range is characteristic of he impedance between a pair of defibrillator electrodes that are properly connected to a defibrillator. For this reason, the routine then generates the enable signal at 252 which is applied to the enable input of the defibrillator 10 to allow the defibrillator 10 to generate a defibrillator pulse.

In the event that the impedance is found at 250 to be greater than 200 ohms, the routine branches to 254 where the measured impedance is compared to 300 ohms. For the routine to reach step 254, the impedance must, of necessity, be larger than 200 ohms. In the event that the impedance is larger than 300 ohms, as determined at 254, the microprocessor 24 switches the impedance measurement circuit 20 to the upper impedance range at 256. In the event that the measured impedance is greater than 200 ohms, but less than 300 ohms, the impedance is characteristic of neither the impedance between a pair of defibrillator electrodes nor the impedance between a pair of patient electrodes. For this reason, the "check electrodes" message is generated at 246.

Assuming that the upper impedance range has now been selected, at the next interrupt the subroutine will branch from 242 to step 258 where the measured impedance is compared to 250 ohms. In the event that the measured impedance is less than 250 ohms, the subroutine causes the impedance measurement circuit 20 to be switched to the lower range at 260. If the impedance is greater than 250 ohms, a comparison is made at 262 to determine if the impedance is less than 300 ohms. If so, the "check electrodes" message is displayed at 246. If the impedance is greater than 300 ohms, the measured impedance is compared to 2k at 264. If the measured impedance is greater than 300 ohms but less than 2k the "monitor only" message is displayed at 268, since an impedance in this range is characteristic of the impedance between a pair of patient monitoring electrodes. If the impedance is found to be greater than 2k at 264, it is likely that the electrode leads 12, 14 are open circuited, i.e., not properly connected to an electrode, so that the "check electrodes" message is once again displayed at 246.

Figure 5:
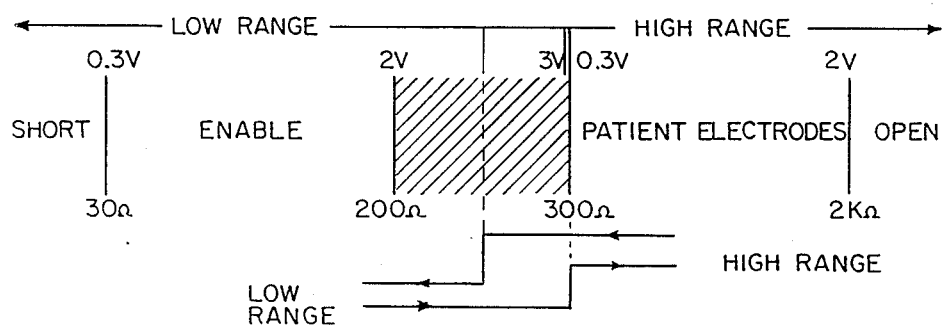
FIG. 5 is a graph showing the operating ranges and range switching points for the impedance measuring circuit of FIG. 3.

The operating ranges and switch points or the microprocessor operating according to the program illustrated in FIG. 4 are illustrated in FIG. 5. When operating in the low impedance range, a measured impedance of less than 30 ohms (i.e., less than 0.3 volt output from the impedance measuring circuit 20) causes a "check electrodes" message to be displayed at 246 (FIG. 4) since the electrode leads are probably short-circuited. Between 30 ohms and 200 ohms (between 0.3 volt and 2 volts from the impedance measuring circuit 20) the enable signal is generated at 252 (FIG. 4) and is applied to the enable input of the defibrillator 10 (FIG. 1). Between 200 and 300 ohms in either the low or the high range, the check electrodes message 246 is displayed, but the impedance measurement is not characteristic of either a short circuit, an open circuit, a defibrillator electrode or a patient electrode. In other words, the results are indeterminate. When operating in the high impedance range, a measured impedance of between 300 ohms and 2k (i.e., an output from the impedance measurement circuit 20 of between 0.3 volt and 2 volts) causes the "monitoring only" message to be displayed at 268, since an impedance in this range is characteristic of the impedance between a pair of patient monitoring electrodes. A measured impedance of greater than 2k (i.e., an output from the measurement circuit 20 of greater than 2 volts) is characteristic of an open circuit and thus causes the "check electrodes" message to be displayed at 246.

In order to prevent the microprocessor 24 from alternately switching between the upper and lower ranges when the impedance measurement is on the borderline between two impedance ranges, the interrupt routine shown in FIG. 4 implements a hysteresis as illustrated in FIG. 5. When an impedance measurement of greater than 300 ohms is made while the measurement circuit 20 is operating in the low impedance range, the microprocessor 24 switches the impedance measurement circuit 20 to the high impedance range. Thereafter, the impedance measurement circuit 20 will remain in the high impedance range even if the measured impedance drops below 300 ohms. The impedance measurement circuit 20 will not be switched back to the low impedance range until the measured impedance in the high impedance range is less than 250 ohms.

It is thus seen that the inventive protective circuit prevents the defibrillator 10 from generating a defibrillator pulse if either the incorrect electrodes are connected to the electrode leads 12, 14 or the electrodes are improperly connected to the electrode leads 12, 14. As a result, the defibrillator 10 can be safely operated by relatively untrained personnel and the defibrillator 10 can operate semiautomatically or even automatically without risk of defibrillating through patient monitoring electrodes or improperly connected electrodes.

We claim:

1. An impedance measurement circuit for measuring an impedance in a device under test, comprising:
   a pair of measurement leads which are adapted to be connected to said device under test;
   an AC current source connected between said measurement leads so that the voltage between said leads is proportional to the impedance of said device under test; and
   an amplifier having a pair of differential inputs connected between said leads, said differential inputs having an input impedance therebetween that is substantially greater than the impedance of said device under test;
   range adjustment means for causing an output signal at the output of said amplifier to have a voltage that is proportional to a relatively large multiple of said impedance in a low impedance range and to a relatively small multiple of said impedance in a high impedance range, thereby increasing the range of said impedance measurement circuit for a predetermined sensitivity and range of output signal voltages; and
   range control means controlling the operation of said range adjusting means, said range control means causing said impedance measurement circuit to initially measure the impedance between said electrodes in said low range and switching said impedance measuring circuit to said high range when the voltage of said output signal is a value indicative of an impedance larger than a first predetermined value.

2. The impedance measurement circuit of claim 1 wherein the frequency of said AC current source is approximately 33 kHz to approximate the impedance between a pair of defibrillation electrodes during a defibrillation pulse.

3. The impedance measurement circuit of claim 1, further including a frequency selection detector connected to the output of said amplifier, said detector generating a DC output signal having a voltage that is proportional to the amplitude of the AC signal at the output of said amplifier.

4. The impedance measurement system of claim 1 wherein said range control means switches said impedance measurement circuit from said high range to said low range when said output signal has a voltage that is a value indicative of an impedance smaller than said first predetermined value.

5. The impedance measurement system of claim 1 wherein said range control means switches said impedance measurement circuit from said high range to said low range when said output signal has a voltage that is a value indicative of an impedance smaller than a second predetermined value, said second predetermined value being substantially less than said first predetermined value, thereby providing hysteresis between the impedance that said impedance measurement circuit switches from said low range to said high range and from said high range to said low range.

6. The impedance measurement circuit of claim 1 wherein said range adjustment means causes said AC current source to apply a relatively large current between said measurement leads in said low impedance range and a relatively small current between said measurement leads in said high impedance range.

* * * * *

UNITED STATES PATENT AND TRADEMARK OFFICE
CERTIFICATE OF CORRECTION

PATENT NO. : 4,870,341

DATED : September 26, 1989

INVENTOR(S) : James M. Pihl; Denny C. Edwards

It is certified that error appears in the above-identified patent and that said Letters Patent is hereby corrected as shown below:

In claim 6, column 12, line 2, delete "current" (first occurrence) and substitute therefor --circuit--.

Signed and Sealed this

Eighteenth Day of September, 1990

Attest:

HARRY F. MANBECK, JR.

*Attesting Officer*   *Commissioner of Patents and Trademarks*